(12) United States Patent
Isham (10) Patent No.: US 8,080,031 B2
(45) Date of Patent: Dec. 20, 2011

(54) MINIMALLY INVASIVE RECTAL BALLOON APPARATUS

(75) Inventor: John Isham, Houston, TX (US)

(73) Assignee: RadiaDyne LLC, Houston, TX (US)

(*) Notice: Subject to any disclaimer, the term of this patent is extended or adjusted under 35 U.S.C. 154(b) by 896 days.

(21) Appl. No.: 12/034,470

(22) Filed: Feb. 20, 2008

(65) Prior Publication Data

US 2008/0200872 A1 Aug. 21, 2008

Related U.S. Application Data

(63) Continuation-in-part of application No. 11/933,018, filed on Oct. 31, 2007, now abandoned, which is a continuation-in-part of application No. 11/623,702, filed on Jan. 16, 2007, now abandoned.

(51) Int. Cl.
*A61M 29/00* (2006.01)

(52) U.S. Cl. ..... 606/197; 606/192; 606/193; 604/103.06

(58) Field of Classification Search ........... 606/197, 606/192, 193, 198, 194, 190; 604/99.01, 604/96.01, 99.02, 100.01, 103.05, 100.02, 604/101.01, 101.02, 103.06, 103.07, 103.08; 600/184, 427

See application file for complete search history.

(56) References Cited

U.S. PATENT DOCUMENTS

| | | | |
|---|---|---|---|
| 3,799,170 A * | 3/1974 | Walsh et al. | 606/193 |
| 5,476,095 A | 12/1995 | Schnall et al. | |
| 7,976,497 B2 | 7/2011 | Shah et al. | |
| 2001/0016729 A1* | 8/2001 | Divino et al. | 604/525 |
| 2003/0028097 A1* | 2/2003 | D'Amico et al. | 600/427 |
| 2005/0267509 A1* | 12/2005 | Davis | 606/193 |
| 2008/0119785 A1* | 5/2008 | Ramsey et al. | 604/98.01 |

OTHER PUBLICATIONS

D'Amico, Anthony V. et al., "A Practical Method to Achieve Prostate Gland Immobilization and Target Verification for Daily Treatment," Int. J. Radiation Oncology Biol. Phys., 2001 pp. 1431-1436, vol. 51 No. 5, © 2001 Elsevier Science Inc., U.S.A. (6 pages).

D'Amico, Anthony V. et al., "A Prospective Evaluation of Rectal Bleeding After Dose-Escalated Three-Dimensional Conformal Radiation Therapy Using an Intrarectal Balloon for Prostate Gland Localization and Immobilization," 2005, Journal Urology, pp. 780-784, vol. 67, No. 4, © 2006 Elsevier Inc. (5 pages).

Little, Darren J. et al., Use of Portal Images and BAT Ultrasonography to Measure Setup Error and Organ Motion for Prostate IMRT: Implications for Treatment Margins, Int'l J. Radiation Oncology Biol. Phys., 2003, pp. 1218-1224, vol. 56, No. 5 © 2003 Elsevier Inc. (7 pages).

(Continued)

*Primary Examiner* — Ryan Severson
*Assistant Examiner* — Tin Nguyen
(74) *Attorney, Agent, or Firm* — Boulware & Valoir (57) ABSTRACT

A rectal balloon apparatus has a shaft with a fluid passageway extending therethrough. A balloon is affixed over an end of the shaft such that the fluid passageway communicates with an interior of the balloon. The balloon has a laterally flat surface thereon when inflated. The laterally flat surface of the balloon has a longitudinal groove formed thereon. The balloon having a pair of bulges formed thereon when the balloon is inflated. A ring is affixed to the shaft adjacent the balloon. The shaft has a plurality of holes formed thereon opening to an interior of the balloon.

12 Claims, 4 Drawing Sheets

OTHER PUBLICATIONS

McGary, John E. et al., Prostate Immobilization Using a Rectal Balloon, Journal of Applied Clinical Medical Physics, 2002, pp. 6-11, vol. 3, No. 1, © 2002 Am. Coll. Med. Phys. (6 pages).

Patel, Rakesh R. et al., "Rectal Dose Sparing with a Balloon Catheter and Ultrasound Localization in Conformal Radiation Therapy for Prostate Cancer," Radiotherapy & Oncology Journal of the European Society for Therapeutic Radiology and Oncology, 2003, pp. 285-294, vol. 67, © 2003 Elsevier Science Ireland Ltd. (10 pages).

Van Lin, Emile N. J. TH. et al., "Rectal Wall Sparing Effect of Three Different Endorectal Balloons in 3D Conformal and IMRT Prostate Radiotherapy," Int'l J. Radiation Oncology Biol. Phys., 2005, pp. 565-576, vol. 63, No. 2 © 2005 Elsevier, Inc. (12 pages).

Poli, M. Esmeralda Ramos et al., An Assessment of PTV Margin Definitions for Patients Undergoing Conformal 3D External Beam Radiation Therapy for Prostate Cancer Based on an Analysis of 10,327 Pretreatment Daily Ultrasound Localizations, Int. J, Radiation Oncology Biol. Phys., 2007, pp. 1430-1437, vol. 67, No. 5, © Elsevier Inc. (8 pages).

Pollack, Alan et al., "Prostate Cancer Radiation Dose Response: Results of the M.D. Anderson Phase III Randomized Trial," Int J. of Radiation Oncology Biol, Phys., 2002, pp. 1097-1105, vol. 53, No. 5, © 2002 Elsevier Science Inc. (9 pages).

Storey, Mark R. et al., "Complications from Radiotherapy Dose Escalation in Prostate Cancer: Preliminary Results of a Randomized Trial," Int J. Radiation Oncology Biol. Phys., 2000, pp. 635-642, vol. 48, No. 3, © 2000 Elsevier Science Inc. (8 pages).

Van Lin, Emile N. J. TH. et al. "Reduced Late Rectal Mucosal Changes After Prostate Three-Dimensional Conformal Radiotherapy with Endorectal Balloon as Observed in Repeated Endoscopy," Int. J. Radiation Oncology Biol. Phys., 2007, pp. 799-811, vol. 67, No. 3, © 2007 Elsevier Inc. (13 pages).

Wang, Zhou et al., "The Effect of Positional Realignment on Dose Delivery to the Prostate and Organs-at-Risk for 3DCRT," Medical Dosimetry, 2007, pp. 1-6, vol. 32, No. 1, © 2007 American Association of Medical Dosimetry (6 pages).

Zietman, A. L. et al., "A Randomized Trial Comparing Conventional Dose (70.2 GyE) and High-Dose (79.2 GyE) Conformal Radiation in Early Stage Adenocarcinoma of the Prostate; Results of an Interim Analysis of RROG 45-09" Int. J. Radiation Oncology Biol. Phys., 2004, pp. S131-S132, vol. 60, No. 1, Supp. 2004, © 2004 Elsevier B. V. (2 pages).

* cited by examiner

# MINIMALLY INVASIVE RECTAL BALLOON APPARATUS

CROSS-REFERENCE TO RELATED U.S. APPLICATIONS

The present application is a continuation-in-part of U.S. application Ser. No. 11/933,018, filed on Oct. 31, 2007 and entitled "Minimally Invasive Rectal Balloon Apparatus", presently pending, which is a continuation-in-part of U.S. application Ser. No. 11/623,702, filed on Jan. 16, 2007 and entitled "Minimally Invasive Rectal Balloon Apparatus", presently pending.

STATEMENT REGARDING FEDERALLY SPONSORED RESEARCH OR DEVELOPMENT

Not applicable.

NAMES OF PARTIES TO A JOINT RESEARCH AGREEMENT

Not applicable.

REFERENCE TO AN APPENDIX SUBMITTED ON COMPACT DISC

Not applicable.

BACKGROUND OF THE INVENTION

1. Field of the Invention

The present invention relates to an apparatus for facilitating performance of diagnostic and therapeutic treatment of disease. Particularly, the present invention relates to rectal balloons that are used for immobilizing the region surrounding the prostate during pre-treatment simulation and target localization, as well as during the delivery of radiation therapy to treat prostate cancer. More particularly, the present invention relates to minimally invasive rectal probes.

2. Description of Related Art Including Information Disclosed Under 37 CFR 1.97 and 37 CFR 1.98

Treatment of prostate cancer using radiation therapy is difficult due to the prostate's position near radiation-sensitive tissues, and is further complicated by prostate motion. Adenocarcinoma of the prostate commonly occurs in the posterior portion of the prostate gland which is in very close proximity to the rectal wall. To date, external beam radiation treatment, urethrograms, CT scans and magnetic resonance imaging (MRI) have all been used to visually localize the prostate, as well as the normal critical structures in the surrounding area.

U.S. Pat. No. 5,476,095, issued on Dec. 19, 1995 to Schnall et al., describes an insertable pickup probe for use in providing diagnostic MRI images. The pickup probe, in its preferred embodiment, is for use in imaging the male prostate and comprises an elongated shaft supporting an inflatable patient interface balloon at its distal end. The interface balloon comprises an inner balloon and an outer balloon, between which a receiving coil is positioned. A lumen for air supply is provided in the shaft for expanding the inner balloon against the outer balloon to place the receiving coil in close proximity to the area of interest in order to provide MRI images.

Typically, the planning of radiation therapy for the treatment of prostate cancer involves the patient undergoing a CT-based simulation scan of the pelvis to determine the location of the prostate gland. In the simulation phase, the patient is placed on CT equipment that is preferably similar to the radiation treatment equipment (except that it does not generate the high energy radiation beam). The simulation equipment is positioned to simulate the delivery of the sequence of treatment beams prescribed by the treating oncologist. Normally, during the simulation procedure, CT images are acquired. These CT images allow the oncologist to locate the position of the tumor and help to facilitate the composition of a radiation treatment plan. This treatment plan delineates the positions of the radiation equipment components for delivery of the treatment beams.

During the actual treatment phase, the patient is placed in the same position on the treatment equipment as in the simulation scans. Radiation-emitting devices are generally known and used for radiation therapy in the treatment of patients. Typically, a radiation therapy device includes a gantry, which can be swiveled around a horizontal axis of rotation in the course of a therapeutic treatment. A linear accelerator is located in the gantry for generating a high-energy radiation beam for therapy. During treatment, the radiation beam is provided by this equipment and is delivered to the patient at the precise location as delineated by the physician during simulation. A further feature of radiation therapy involves portal images, which are commonly used in radiation therapy to verify and record the patient tumor location. Portal images include manual (film) and electronic images (EPI) taken before and/or after the treatment.

During external beam radiation therapy, radiation is directed to the target prostate which is near the rectal wall. A misdirected radiation beam may perforate the rectal wall causing radiation proctitis (rectal bleeding). This toxicity is related to the total radiation dose prescribed and the volume of the anterior rectal wall receiving a high radiation dose. A major factor limiting radiation oncologists' attempts to reduce the volume of the anterior rectal wall receiving a high radiation dose is the position of the prostate gland as well as the intrinsic motion up to 5 mm in the anterior to posterior direction caused by rectal peristalsis. Accordingly, oncologists generally will add a margin to the radiation field in order to ensure that the entire prostate gland receives the prescription dose. This margin is typically on the order of 5 to 15 mm. As a consequence, lower doses of radiation may need to be used so as not to overexpose radiation sensitive structures. However, this may lead to inadequate radiation treatment and a higher probability of local cancer recurrence.

U.S. Patent Publication No. 2003/0028097, published on Feb. 6, 2003 to D'Amico et al., describes an immobolizer probe system and method. This system has an insertable probe for immobilizing a region of interest during staging and radiation therapy thereof. In particular, this device uses a balloon having a rectangular cross section connected to a shaft. The shaft extends to an end of the balloon so as to allow fluid flow through an interior of the shaft and into the balloon so as to selectively inflate the balloon once the balloon is installed into the rectal cavity. The balloon, shaft and handle are bonded together so that they move radially as a single unit when torque is applied. A syringe is provided which connects the shaft and serves as an air pump to deliver a volume-limited amount of air to the air lumen of the shaft to the balloon. A stop cock is provided to maintain the air within the balloon.

One of the problems with the subject of U.S. Patent Publication No. 2003/0028097 is the discomfort associated with installing the rectal balloon within the rectal cavity. In particular, a relatively sturdy and wide diameter shaft is connected to a relatively large thick-walled balloon. Because the balloon is not supported by anything other than by the shaft, the balloon is formed of a relatively rugged and thick material. Because of the relatively large size of the shaft and the thick material of the rectangular-cross section balloon, the installation of the rectal balloon creates a large amount of discomfort for a patient. It is often difficult for the medical personnel to know exactly how far within the rectum the balloon has been installed. It is difficult to achieve a standardized and fixed position of the balloon during each and every use. The medical personnel must generally approximate the desired position of the balloon within the rectal cavity. As such, a need has developed whereby the rectal balloon can be formed of a minimal diameter shaft and of a balloon of relatively thin material.

When the rectal balloon of U.S. Patent Publication No. 2003/0028097 is in an inflated condition, the outer surface is generally round. As such, the prostate will tend to balance on the curved surface rather than be properly seated thereon. Since seating is important for proper use, this device requires that the physician approximate a seated position rather than providing any feedback of the seated position. When the balloon is in a curved inflated condition, the prostate will have a tendency to slide to one side of the balloon. As such, a need developed to provide a rectal balloon that retains the prostate in a proper seated position when the balloon is in a fully inflated condition.

The inventor is also the owner of U.S. application Ser. No. 11/623,702 ("the '702 application"), filed on Jan. 16, 2007, and U.S. application Ser. No. 11/933,018 ("the '018 application), filed on Oct. 31, 2007. The '018 application is a continuation-in-part of the '702 application. Each of these applications describe a rectal balloon apparatus similar to that of the present invention. Both the '702 and the '018 applications described a sleeve positioned over the balloon when the balloon is in the uninflated condition. The sleeve maintains the balloon in a tightly juxtaposed position against the shaft for a minimal profile for insertion into the rectum. Additionally, the '018 application describes the sleeve as having a frangible seam such that it can be torn away as it is pulled away from the balloon. During experimentation, it was found that the sleeve was not always necessary.

Experimentation also showed that the shape of the surface of the balloon which engages the prostate was of great importance. The '702 application did not discuss the shape in great detail, but did contemplate a seating area for the prostate to be positioned on. The '018 application expanded on that idea and described two different inflated conditions of the balloon, each with a unique shape. In the first inflated condition, the balloon has a laterally flat seating area on which the prostate rests. When additional fluid is added to the balloon, it moves to the second inflated condition. In the second inflated condition, the balloon has a laterally flat seating area and a bulbous portion formed at the end of the balloon adjacent to the tip. The bulbous portion works against the natural forces seeking to expel the balloon from the rectum. The location of this bulge serves to contour the seminal vesicles in proper alignment.

It is an object of the present invention to provide a rectal balloon apparatus which is easy to use and easy to install.

It is another object of the present invention to provide a rectal balloon apparatus whereby the position of the balloon can be easily ascertained by medical personnel.

It is a further object of the present invention to provide a rectal balloon apparatus which maximizes the comfort of the patient.

It is a further object of the present invention to provide a rectal balloon apparatus which has improved holding stability when inflated.

It is a further object of the present invention to provide a rectal balloon apparatus which has a flexible shaft.

It is another object of the present invention to provide a rectal balloon apparatus which can be inflated to several configurations for different medical purposes.

It is another object of the present invention to provide a rectal balloon apparatus which enhances the ability to properly seat the prostate on a flat surface of the rectal balloon.

It is a further object of the present invention to provide a rectal balloon apparatus which avoids potential allergic reactions.

It is still a further object of the present invention to provide a rectal balloon apparatus which is easy to manufacture and relatively inexpensive.

It is still another object of the present invention to provide a rectal balloon apparatus which uniformly displaces the anal verge.

It is a further object of the present invention to provide a rectal balloon apparatus that facilitates the removal of fluid from the interior of the balloon.

It is a further object of the present invention to provide a rectal balloon apparatus that provides a visual indication of when the balloon is positioned beyond the anal verge.

These and other objects and advantages of the present invention will become apparent from a reading of the attached specification and appended claims.

BRIEF SUMMARY OF THE INVENTION

The present invention is a rectal balloon apparatus that comprises a shaft having a fluid passageway extending therethrough and a balloon affixed over an end of the shaft such that the fluid passageway communicates with an interior of the balloon. The balloon is movable from a non-inflated condition to a first inflated condition and to a second inflated condition. The balloon has a generally laterally flat surface when in the first inflated condition. In the second inflated condition, the balloon has both a laterally flat surface and a bulge extending outwardly of the laterally flat surface adjacent a distal end of the shaft. The balloon is movable from the second inflated condition to a third inflated condition. In a third inflated condition, the balloon has a second bulge extending outwardly of the laterally flat surface at an opposite end of the balloon from the first bulge. The second bulge is adjacent an end of the balloon opposite a tip of the balloon.

In the present invention, a groove is formed in the laterally flat surface. The groove extends longitudinally along a portion of the laterally flat surface. The groove has a generally rectangular shape. The balloon has a generally V-shaped end portion. The shaft is made of a flexible material. There is a valve means affixed to the shaft at an end opposite the balloon. The valve means is for selectively allowing a fluid to pass through the shaft and to the balloon so as to move the balloon from a non-inflated condition to an inflated condition. The valve means has a port thereon. A fluid introducing means is removably connected to the port and can move the balloon from a non-inflated condition to an inflated condition. The non-inflated condition can be a vacuum such that the balloon resides tightly over the shaft. The shaft has a plurality of holes formed therein in an area surrounded by the balloon. Each of the holes is offset by 90° from an adjacent hole. An indicator ring is affixed to the exterior of the shaft adjacent an end of the balloon. The indicator ring is of a color so as to provide a positive indication of when the balloon is past the anal verge.

The present invention is also a method of positioning a prostate for radiation therapy or other treatment. The method comprises the steps of forming a balloon affixed to a shaft, inserting the balloon in an uninflated condition into a patient's rectum, positioning the balloon against the patient's prostate, and inflating the balloon so as to form a generally laterally flat surface for the prostate to rest upon. The method also comprises further inflating the balloon so as to form both a generally laterally flat surface and a bulge extending outwardly of the laterally flat surface. The method can also comprise even further inflating the balloon so as to form a second bulge extending outwardly of the laterally flat surface at an opposite end of the balloon from the first bulge.

DETAILED DESCRIPTION OF THE INVENTION

Figure 1:
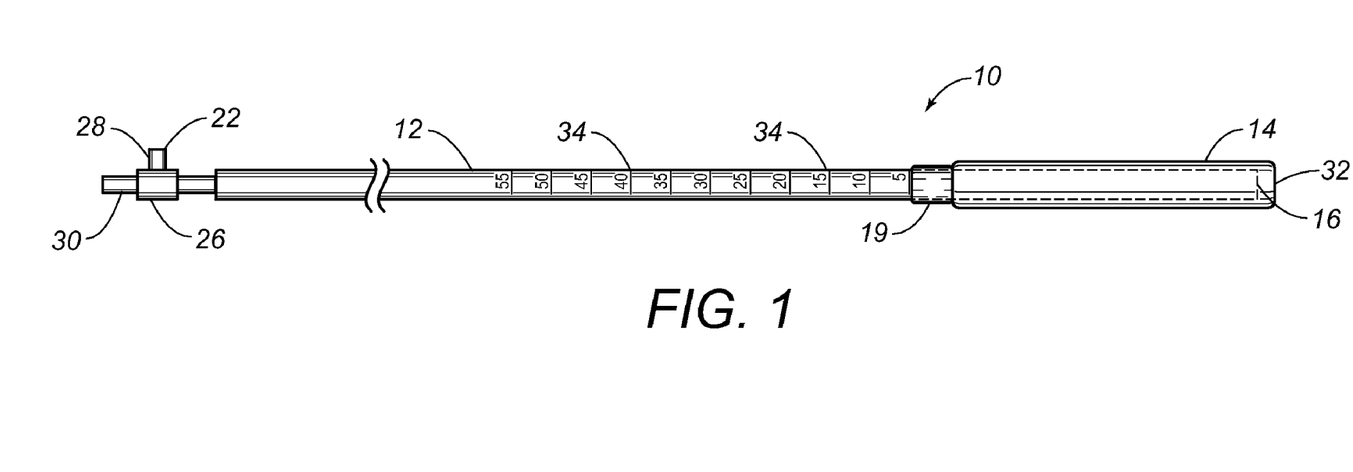
FIG. 1 is a side elevational view, partially transparent, which shows the rectal balloon apparatus in an uninflated condition.

Referring to FIG. 1, there is shown the rectal balloon apparatus 10 in accordance with the preferred embodiment of the present invention. The rectal balloon apparatus 10 includes a shaft 12 having a fluid passageway extending therethrough. A balloon 14 is affixed over the end 16 of the shaft 12. The balloon 14 is shown in an uninflated condition. The fluid passageway of the shaft 12 can communicate with the interior of the balloon 14.

The shaft 12 is a generally longitudinal shaft which has the fluid passageway extending through the center thereof. The shaft 12 is made of a flexible material. A valve assembly 22 is affixed to the shaft 12 opposite the balloon 14. The valve assembly 22 can have a variety of configurations. FIG. 1 illustrates the valve assembly 22 as an inline valve assembly configuration. The valve assembly 22 may also be an angled valve assembly configuration. The valve assembly 22 includes a stop cock 26. A valve 28 facilitates the ability of the stop cock 26 to open and close so as to selectively allow the fluid to pass into the shaft 12. A port 30 allows the valve assembly 22 to be connected to a supply of the fluid. When the stop cock 26 is opened by the rotation of the valve 28, the fluid will flow through the valve assembly 22, through the interior passageway of the shaft 12 and into the interior of the balloon 14. The valve 28 can then be closed so as to maintain the inflated configuration of the balloon 14. When the procedure is finished and the fluid needs to be removed from the balloon 14, the valve 28 of stop cock 26 can then be opened so as to allow for the release of fluid therethrough.

The opposite end 16 of the shaft 12 contacts the end 32 of the balloon 14. The end 16 is suitably curved or dome-shaped so as to allow the shaft 12 to facilitate the introduction of the balloon 14 into the rectal cavity. The shaft 12 has indicia 34 formed therealong. It can be seen that the indicia 34 has numerical references associated therewith. These numerical references are indicative of the distance that the balloon 14 has been inserted into the rectum. As such, the indicia 34 provide a clear indication to the medical personnel of the desired location of the rectal balloon 14. A ring 19 is affixed to the shaft 12 adjacent to the balloon 14. This ring 19 can be of a bright color, such as blue, so as to provide the medical personnel with positive indication of when the balloon 14 is past the anal verge. The ring 19 is approximately 5 millimeters long.

Figure 2:
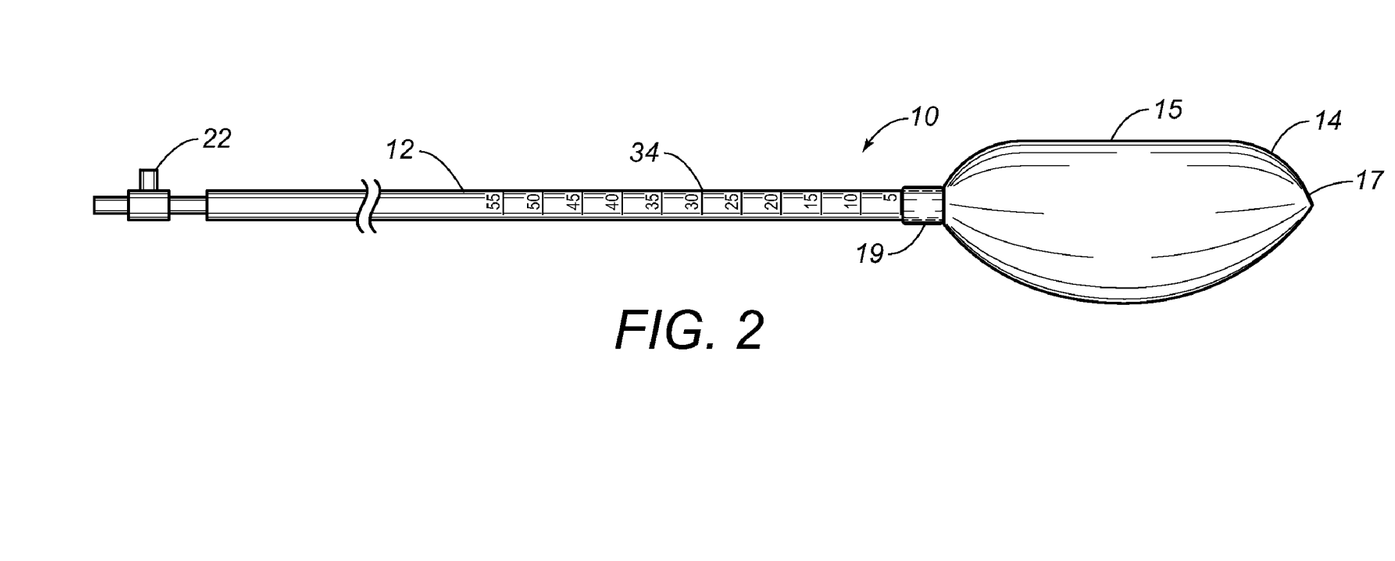
FIG. 2 is a side elevational view of the rectal balloon apparatus of the present invention in the first inflated condition.

FIG. 2 illustrates the apparatus 10 after being installed within the rectum. The fluid can be introduced through the valve assembly 22 and through the interior passageway of the shaft 12 so as to inflate the balloon 14. The ring 19 is shown as adjacent an end of the balloon 14. The balloon 14 has a seating area 15 so that the prostate can be properly positioned thereon. The balloon 14 is shown in the first inflated condition. The balloon 14 has a head portion 17 adjacent the tip of the balloon 14 opposite the shaft 12. When the balloon 14 is installed and inflated, the prostate will reside on the flat surface 15 in a seated position. The head portion 17 will abut the tip of the prostate. After the procedure has been completed, the balloon 14 can be deflated and easily pulled outwardly of the rectum in its deflated condition.

Figures 3, 4, 5:
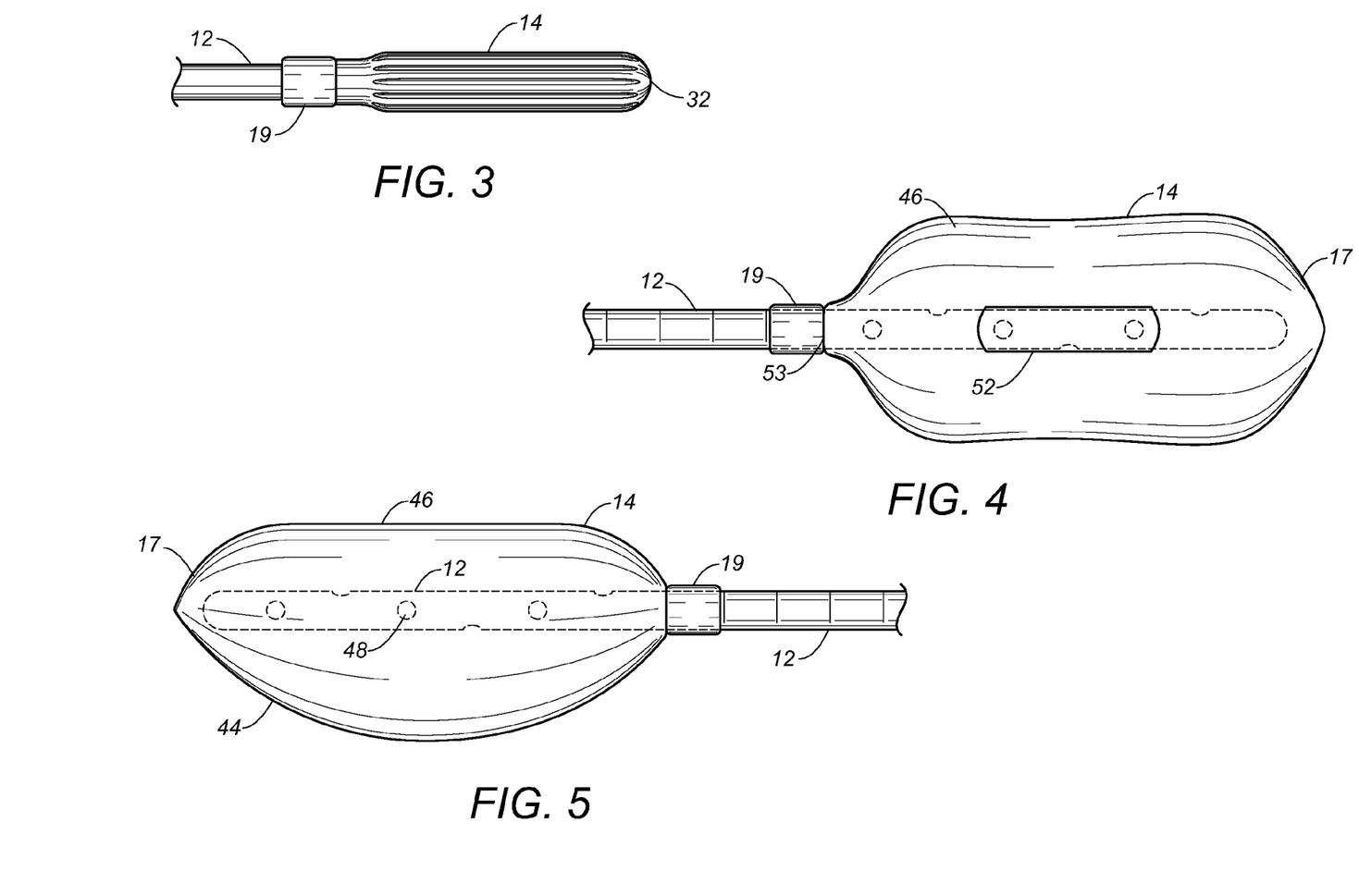
FIG. 3 is an isolated view showing the compact folding of the balloon over the end of the shaft.
FIG. 4 is a top view of the inflated balloon as used in the rectal balloon apparatus of the present invention.
FIG. 5 is a side view, partially transparent, of the balloon of the rectal balloon apparatus in the first inflated condition.

FIG. 3 shows that the balloon 14 is neatly folded and compressed over the outer diameter of the shaft 12. The shaft 12 will have a rounded end abutting the end 32 of the balloon 14. As such, a comfortable rounded profile is provided at this end 32. The end 32 of the balloon 14 is sealed over the outer diameter of the shaft 12. The balloon 14 is pre-vacuumed during production to produce a minimal profile during use. The ring 19 is placed over the shaft 12.

FIG. 4 is a top view of the balloon 14 from the side of the balloon 14 which engages with the prostate. Central seating area 46 is shown as having a groove 52 formed thereon. The groove 52 is generally rectangularly-shaped and engages with the tip of the prostate, reducing lateral motion. The central seating area 46 and the groove 52 enhance the holding stability of the balloon 14 of the present invention. In FIG. 4, it can also be seen that head portion 17 of the balloon 14 is generally V-shaped. This shape makes insertion of the balloon 14 into the rectum easier for medical personnel and more comfortable for the patient. The balloon 14 has a thermally welded bond 53 connecting it to the shaft 12.

FIG. 5 is an isolated view of the balloon 14 as inflated to a first inflated condition. In this first condition, the balloon 14 has a central seating portion 46, a head portion 17 and a bottom portion 44. When inflated, the central seating area 46 has a lateral flatness for the prostate to rest upon. The first inflated condition is formed when approximately 100 cc of fluid are introduced into the balloon 14. The lateral flatness of the seating area 46 will prevent the prostate from sliding to one side or the other. The bottom portion 44 is rounded and contacts the rectal wall. The head portion 17 is generally V-shaped so as to facilitate easier insertion of the balloon 14. The material of the balloon 14 is formed of a non-latex material so as to avoid allergic reactions. The shaft 12 is shown extending into the interior of the balloon 12. A plurality of holes 48 are formed in the shaft 12 through which the balloon 14 is filled with fluid. The plurality of holes 48 are formed within the balloon 14 so as to allow fluid to be introduced into and removed from the balloon 14. To cam be seem that each of the holes 48 is spaced from and offset by 90° from an adjacent hole around the diameter of shaft 12. A total of six holes are formed in the shaft 12 within balloon 14 so as to allow the fluid to pass from an interior of shaft 12 to the interior of the balloon 14. This arrangement of holes 48 facilitates complete extraction of the fluid from the balloon 14. Under certain circumstances, one of the holes may become clogged or blocked by contact between the body and the balloon, the staged arrangement assures that the unblocked holes 48 allow the fluid to continue to be easily extracted.

Figures 6, 7, 8:
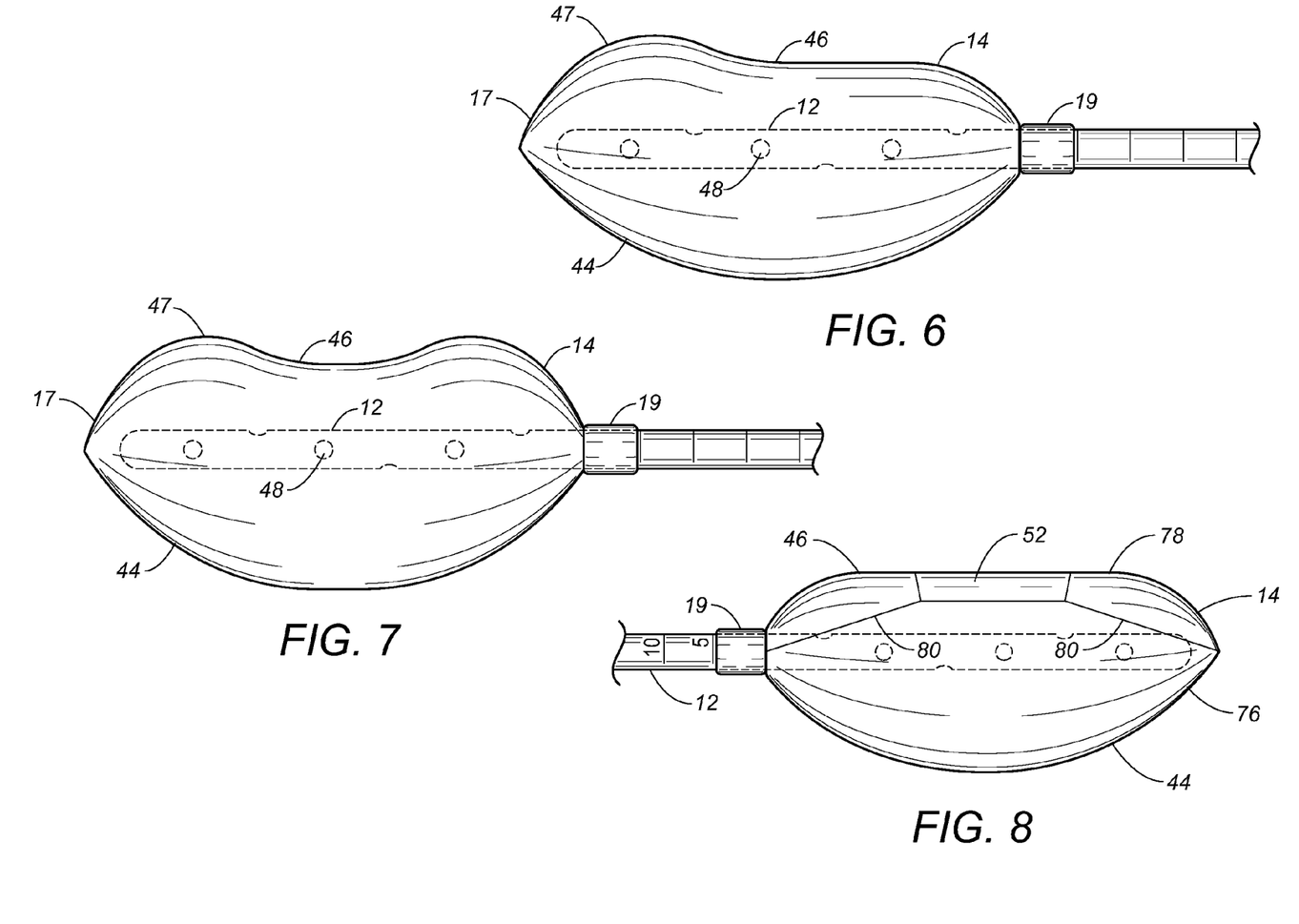
FIG. 6 is a side view, partially transparent, of the balloon of the rectal balloon apparatus in the second inflated condition.
FIG. 7 is side view, partially transparent, of the balloon of the rectal balloon apparatus in the third inflated condition.
FIG. 8 is a cross-sectional side view of the balloon of the rectal balloon apparatus showing the plurality of layers which form the balloon.

FIG. 6 is an isolated view of the balloon 14 as inflated to a second inflated condition. In the second inflated condition, the balloon 14 has a first bulge 47 formed at the head portion 17. The balloon also has a laterally flat seating portion 46. The first bulge 47 can be utilized in certain conditions to better isolate the prostate. Generally, the first bulge 47 will be formed when at least 110 cc of fluid are introduced into the balloon 14.

FIG. 7 is an isolated view of the balloon 14 in a third inflated condition. The third inflated condition can occur simultaneously with the second inflated condition or with the addition of additional fluid into the balloon 14. In the third inflated condition, the balloon has a second bulge 49 formed opposite to the head portion 17. In the third inflated condition, the balloon maintains the first bulge 47 and the laterally flat seating portion 46. The second bulge 49 can be utilized to enhance the isolation of the prostate. Additionally, the first and second bulges work against the body's natural forces which seek to expel the balloon from the rectum. The first bulge 47 serves to properly contour the seminal vesicles above the prostrate. The proper contour is maintained during displacement of the balloon. The second bulge 49 allows a uniform displacement of the healthy tissues adjacent the anal verge. This serves to address the tighter margins formed in the area of the anal verge.

FIG. 8 is a cross-sectional side view of the balloon 14, showing the plurality of layers which form the balloon 14. A bottom layer 76 forms the bottom portion 44 of the balloon 14. A top layer 78 forms the upper portion, including central seating area 46 and the groove 52, of the balloon 14. A middle layer 80 extends between the bottom layer 76 and the top layer 78. The middle layer 80 is connected to the top layer 78 at the groove 52.

Figure 9:
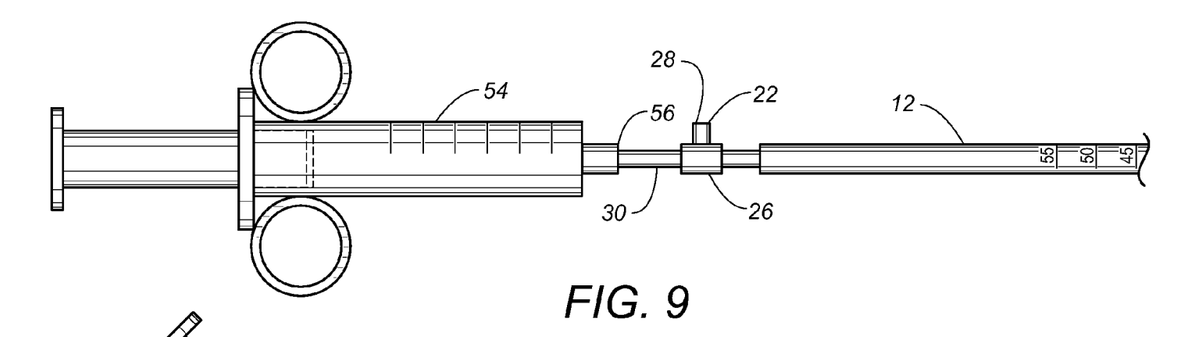
FIG. 9 is an isolated view showing the valve assembly of the rectal balloon apparatus in an aligned configuration.

FIG. 9 shows an isolated view of the shaft 12 of the rectal balloon apparatus 10 at an end opposite the balloon 14. The valve assembly 22 is shown in an inline configuration. The valve assembly 22 is connected at one end to the shaft 12 and at the opposite end to a fluid introducing device 54. In this case, the fluid introducing device 54 is a syringe. The syringe 54 serves as a removable handle for the rectal balloon apparatus 10. An end portion 56 of the syringe 54 is removably connected to the port 30 of the valve assembly 22. When the valve 28 and the stop cock 26 are in an open position, fluid can travel from the syringe 54 into the shaft 12 and to the balloon 14. With the balloon 14 inflated, the valve assembly may be closed and the syringe 54 removed. The syringe 54 can be reconnected to the valve assembly 22 prior to removal of the balloon 14 from the rectum to aid in removing the fluid from the balloon 14.

Figure 10:
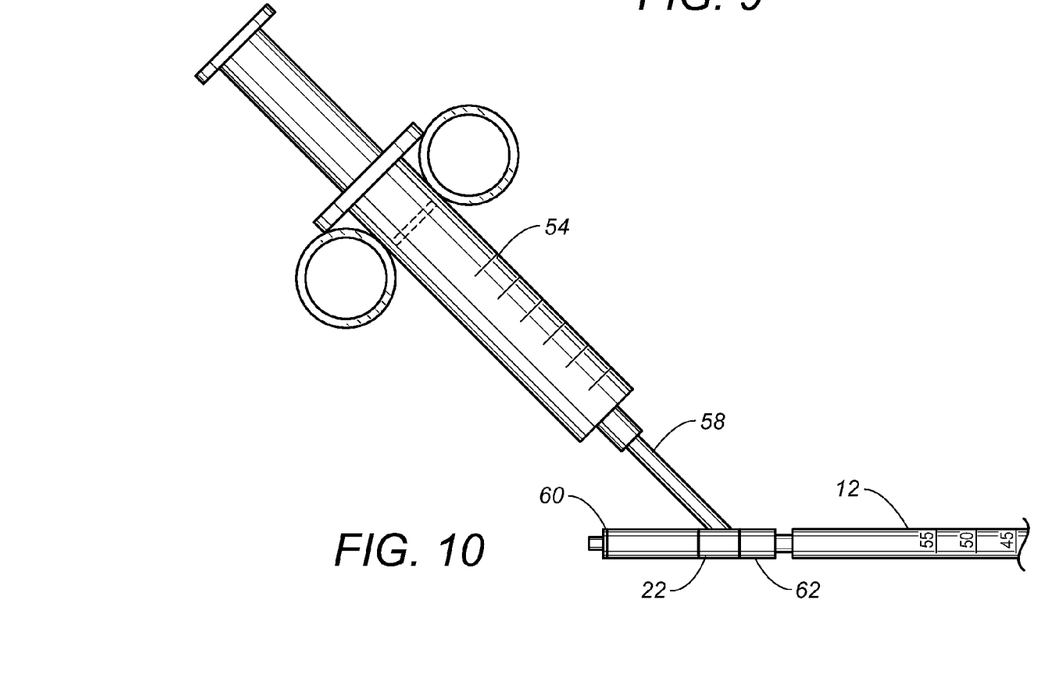
FIG. 10 is an isolated view showing the valve assembly of the rectal balloon apparatus in an angled configuration.

FIG. 10 also shows an isolated view of the shaft 12 of the rectal balloon apparatus 10 at an end opposite the balloon 14. Here, the valve assembly 22 is shown in an angled configuration. The angled configuration may be utilized to give the apparatus a smaller profile. The valve assembly 22 in the angled configuration is connected at one end to the shaft 12 and is closed at an opposite end 60. A port 58 extends at approximately a 45° angle relative to the shaft 12 in a direction away from the balloon 14. A syringe 54 is removably attached to the connector 58. A valve 62 is located on the valve assembly 22 in a position between the connector 58 and the shaft 12. With the valve 62 in an open position, fluid may be passed into or out of the shaft 12 and the balloon 14.

The foregoing disclosure and description of the invention is illustrative and explanatory thereof. Various changes in the details of the illustrated construction can be made within the scope of the present claims without departing from the true spirit of the invention. The present invention should only be limited by the following claims and their legal equivalents.

I claim:

1. A prostate immobilizing rectal balloon, said rectal balloon comprising:
   a. a flexible shaft having a fluid passageway extending therethrough and having a distal end and a proximal end,
   b. one balloon having an upper portion, a bottom portion, a distal end near said distal end of said shaft and a proximal end that is affixed to said shaft, such that said fluid passageway communicates with an interior of said balloon,
   c. wherein said balloon comprises a top layer connected to a bottom layer to form said balloon,
   d. said balloon further comprising a middle layer extending between said top layer and said bottom layer, wherein said middle layer is connected to said top layer at a groove,
   e. wherein said balloon has a first inflated position wherein said upper portion is generally laterally flat and said bottom portion is rounded, said groove forming a central seating area that is configured to engage with a prostate when inflated,
   f. wherein said balloon has a second further inflated position wherein said upper portion has a bulge at said distal end of said balloon,
   g. wherein said bulge is configured to immobilize said prostate in position at said groove.

2. The prostate immobilizing rectal balloon of claim 1, wherein said balloon has a third further inflated condition wherein said upper portion has a second bulge at said proximal end of said balloon.

3. The prostate immobilizing rectal balloon of claim 1, groove extending centrally longitudinally along a portion of said laterally flat surface.

4. The prostate immobilizing rectal balloon of claim 1, said groove having a generally rectangular shape.

5. The prostate immobilizing rectal balloon of claim 1, said shaft having a ring extending therearound proximally adjacent to said balloon.

6. The prostate immobilizing rectal balloon of claim 1, said shaft having a plurality of holes formed therein communicating with an interior of said balloon, each hole being spaced from and offset from an adjacent hole.

7. The prostate immobilizing rectal balloon of claim 1, further comprising a handle affixed to said proximal end of said shaft.

8. The prostate immobilizing rectal balloon of claim 7, said handle having a flexible tube connecting thereto, said tube communicating with said fluid passageway of said shaft.

9. The prostate immobilizing rectal balloon of claim 1, said balloon being formed of a non-latex material.

10. The prostate immobilizing rectal balloon of claim 1, said balloon being tightly juxtaposed over said shaft in said non-inflated condition.

11. The prostate immobilizing rectal balloon of claim 1, said shaft having indicia formed on an exterior surface thereof for marking a position of said balloon.

12. The prostate immobilizing rectal balloon of claim 1, said shaft including a stop cock to maintain the inflated position of said balloon.

* * * * *